United States Patent [19]

Bachmann et al.

[11] Patent Number: 5,683,965

[45] Date of Patent: Nov. 4, 1997

[54] SUBSTITUTED ARYL KETO-ENOLIC HETEROCYCLES

[75] Inventors: Jürgen Bachmann, Weinheim an der Bergstrasse; Thomas Bretschneider, Lohmar; Reiner Fischer, Monheim; Bernd-Wieland Krüger, Bergisch Gladbach; Hans-Joachim Santel; Markus Dollinger, both of Leverkusen; Christoph Erdelen, Leichlingen; Ulrike Wachendorff-Neumann, Neuwied, all of Germany

[73] Assignee: Bayer Aktiengesellschaft, Leverkusen, Germany

[21] Appl. No.: 569,194

[22] PCT Filed: Jun. 22, 1994

[86] PCT No.: PCT/EP94/02042

§ 371 Date: May 13, 1996

§ 102(e) Date: May 13, 1996

[87] PCT Pub. No.: WO95/01971

PCT Pub. Date: Jan. 19, 1995

[30] Foreign Application Priority Data

Jul. 5, 1993 [DE] Germany ............... 43 22 273.0
Apr. 20, 1994 [DE] Germany ............... 44 13 669.2

[51] Int. Cl.$^6$ ............... A01N 43/56; A61K 31/415; C07D 237/26
[52] U.S. Cl. ............... 504/238; 504/284; 504/299; 514/405; 514/413; 514/462; 544/235; 548/453; 549/265
[58] Field of Search ............... 549/265, 304, 549/305, 315; 514/462, 413, 405, 461, 464, 471, 473, 409, 404; 504/299, 284, 238; 548/453, 408, 410, 544, 302.1, 302.7, 302.4, 316.7; 544/235, 234, 236

[56] References Cited

U.S. PATENT DOCUMENTS

| | | | |
|---|---|---|---|
| 4,985,063 | 1/1991 | Fischer et al. | 71/88 |
| 5,045,560 | 9/1991 | Fischer et al. | 514/425 |
| 5,091,537 | 2/1992 | Fischer et al. | 546/226 |
| 5,094,681 | 3/1992 | Kramer et al. | 71/88 |
| 5,116,836 | 5/1992 | Fischer et al. | 514/224.2 |
| 5,142,065 | 8/1992 | Fischer et al. | 548/533 |
| 5,186,737 | 2/1993 | Fischer et al. | 504/283 |
| 5,191,089 | 3/1993 | Baasner et al. | 548/550 |
| 5,225,434 | 7/1993 | Bertram et al. | 514/411 |
| 5,258,527 | 11/1993 | Krauskopf et al. | 548/543 |
| 5,262,383 | 11/1993 | Fischer et al. | 504/195 |
| 5,288,874 | 2/1994 | Santel et al. | 548/453 |
| 5,304,530 | 4/1994 | Cliff et al. | 504/266 |
| 5,332,720 | 7/1994 | Kruger et al. | 504/281 |
| 5,474,974 | 12/1995 | Kruger et al. | 504/236 |
| 5,504,057 | 4/1996 | Fischer et al. | 504/283 |

FOREIGN PATENT DOCUMENTS

| | | |
|---|---|---|
| 0355599 | 2/1990 | European Pat. Off. |
| 0508126 | 10/1992 | European Pat. Off. |
| 0528156 | 2/1993 | European Pat. Off. |
| 4014420 | 4/1991 | Germany |
| 4213026 | 10/1993 | Germany |

*Primary Examiner*—Joseph McKane
*Assistant Examiner*—Richard S. Myers, Jr.
*Attorney, Agent, or Firm*—Sprung Kramer Schaefer & Briscoe

[57] ABSTRACT

The aryl-keto-enolic heterocycles according to the invention have the formula (I), in which Het stands for a heterocyclic group from the series (a), (b) or (c), and X, Y, Z, n, A, B, E, L and M have the meanings given in the description. The compounds having the formula (I) are pesticides, in particular acaricides, insecticides, fungicides and herbicides. Also disclosed is their preparation.

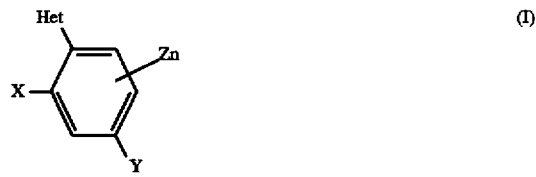

(I)

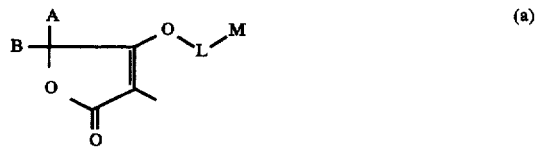

(a)

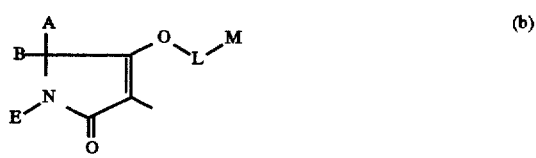

(b)

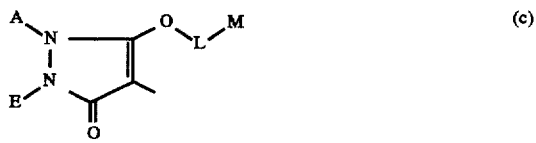

(c)

13 Claims, No Drawings

SUBSTITUTED ARYL KETO-ENOLIC HETEROCYCLES

This is a filing under 35 U.S.C. § 371 of PCT/EP94/02042, filed Jun. 22, 1994.

The present invention relates to novel substituted aryl keto-enolic heterocycles, to a number of processes for their preparation and to their use as pesticides.

It is known that certain substituted $\Delta^3$-dihydrofuran-2-one derivatives possess herbicidal properties (cf. DE-A 4 014 420). The synthesis of the tetronic acid derivatives (such as for example 3-(2-methyl-phenyl)-4-hydroxy-5-(4-fluorophenyl)$\Delta^3$-dihydrofuran-2-one) used as starting compounds is likewise described in DE-A 4 014 420. Compounds of similar structure, without the indication of insecticidal and/or acaricidal activity, are known from the publication Campbell et al., I. Chem. Soc., Perkin Trans. 1 1985, (8) 1567–76.

Pharmaceutical properties have been described previously for 3-acyl-pyrrolidine-2,4-diones (S. Suzuki et al. Chem. Pharm. Bull. 15 1120 (1967)). Furthermore, N-phenyl-pyrrolidine-2,4-diones have been synthesized by R. Schmierer and H. Mildenberger (Liebigs Ann. Chem. 1985 1095). A biological activity of these compounds has not been described.

EP-A 0 262 399 discloses compounds of similar structure (3-aryl-pyrrolidine-2,4-diones) for which, however, no herbicidal, insecticidal or acaricidal action has become known. Known to have a herbicidal, insecticidal or acaricidal action are unsubstituted, bicyclic 3-aryl-pyrrolidine-2,4-dione derivatives (EP-A 355 599 and EP 415 211), substituted bicyclic 3-aryl-pyrrolidine-2,4-dione derivatives (EP 501 129) and substituted mono-cyclic 3-aryl-pyrrolidine-2,4-dione derivatives (EP-A 377 893, EP 442 077 and EP 497 127).

Polycyclic 3-aryl-pyrrolidine-2,4-dione derivatives (EP-A442 073), 1H-3-aryl-pyrrolidine-dione derivatives (EP 456 063 and EP 521 334) and substituted bicyclic 3-aryl-pyrrolidine-dione derivatives (EP 501 129) are also known.

Also known are tetronic acid derivatives having fungicidal, herbicidal, acaricidal and insecticidal properties (EP 528 156). 4-Arylpyrazolidine-dione derivatives having herbicidal, acaricidal and insecticidal properties are described in WO 92/16510 and EP 508 126.

Novel substituted aryl keto-enolic heterocycles have now been found of the formula (I)

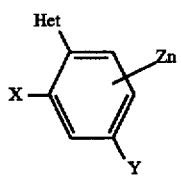

(I)

in which

X represents alkyl, halogen or alkoxy,

Y represents hydrogen, alkyl, halogen, alkoxy or halogenoalkyl,

Z represents alkyl, halogen or alkoxy, n represents a number 0, 1, 2 or 3,

Het represents a heterocyclic group from the series

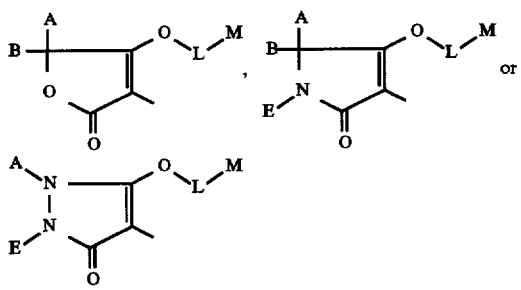

A and B can be identical or different and represent hydrogen, in each case optionally halogen-substituted alkyl, alkenyl, alkoxyalkyl, alkylthioalkyl, cycloalkyl which is optionally interrupted by at least one heteroatom, or aryl, aralkyl or hetaryl each of which is optionally substituted by halogen, alkyl, halogenoalkyl, alkoxy, halogenoalkoxy or nitro, or in which A and B, together with the carbon atom to which they are attached, form a saturated or unsaturated ring which is optionally interrupted by at least one heteroatom and is optionally substituted, E represents hydrogen, in each case optionally halogen-substituted alkyl, alkenyl, alkoxyalkyl, alkylthioalkyl, cycloalkyl which is optionally interrupted by at least one heteroatom, or aryl, aralkyl or hetaryl each of which is optionally substituted by halogen, alkyl, halogenoalkyl, alkoxy, halogenoalkoxy or nitro, or in which A and E, together with the atoms to which they are attached, form a saturated or unsaturated monocyclic, bicyclic or tricyclic ring system which is optionally interrupted by at least one heteroatom and is optionally substituted, L represents an alkanediyl group, M represents one of the following groups:

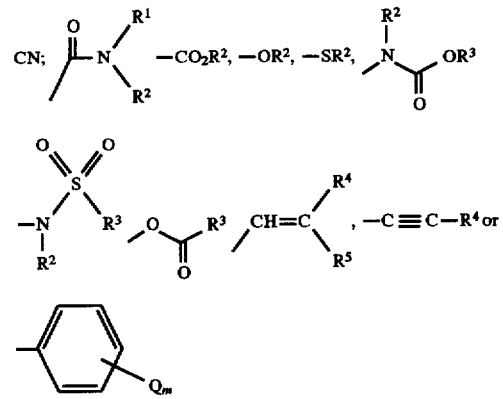

in which $R^1$ represents hydrogen or alkyl, $R^2$ represents in each case optionally substituted alkyl, alkenyl, alkinyl, cycloalkyl, alkoxyalkyl, alkylthioalkyl, aryl or aralkyl, $R^3$ represents optionally substituted alkyl, aryl or aralkyl, $R^4$ represents hydrogen, halogen, in each case optionally substituted alkyl or phenyl, $R^5$ represents hydrogen, halogen or optionally substituted alkyl, Q represents halogen, alkyl, alkoxy, halogenoalkyl, halogenoalkoxy, CN or nitro, and m represents a number 0, 1, 2 or 3, and the enantiomerically pure forms of compounds of the formula (I).

Depending on the substituents, the compounds of the formula (I) can be present as geometrical and/or optical isomers or isomer mixtures of varying compositions. Both the pure isomers and the isomer mixtures, the preparation and use thereof, and compositions comprising them are part of the claimed invention. However, for the sake of simplicity the text below refers always to compounds of the formula (I) although what is meant are both the pure compounds and, if appropriate, mixtures with varying proportions of isomeric compounds.

It has also been found that the novel compounds of the formula (I) have a very good activity as pesticides, preferably as arthropodicides, fungicides and herbicides.

It additionally been found that the novel substituted aryl keto-enolic heterocycles of the formula (Ia)

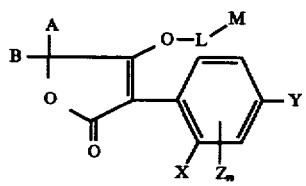
(Ia)

in which

A, B, L, M, X, Y, Z and n have the meaning given above are obtained if (A) Compounds of the formula (IIa)

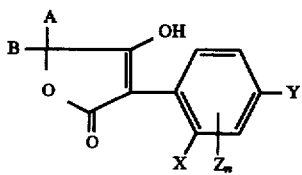
(IIa)

in which

A, B, X, Y, Z and n have the meaning given above are reacted with compounds of the formula (III)

G—L—M (III)

in which

L and M have the meaning given above
and

G represents a leaving group, such as halogen, sulphonylalkyl or sulphonylaryl in the presence of a diluent and in the presence of a base.

(B) in addition, compounds of the formula (Ib)

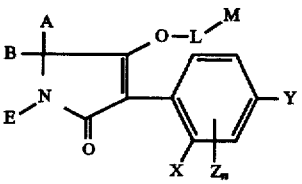
(Ib)

in which

A, B, E, L, M, X, Y, Z and n have the meaning given above are obtained if compounds of the formula (IIb)

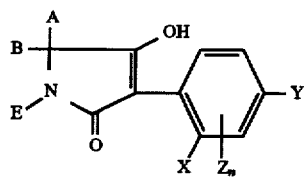
(IIb)

in which

A, B, E, X, Y, Z and n have the meaning given above are reacted with compounds of the formula (III)

G—L—M (III)

in which

L and M have the meaning given above
and

G represents a leaving group, such as halogen, sulphonylalkyl or sulphonylaryl, in the presence of a diluent and in the presence of a base.

(c) Moreover, compounds of the formula (Ic)

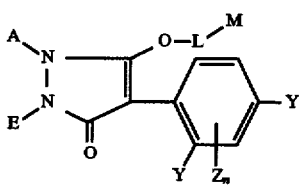
(Ic)

in which

A, E, L, M, X, Y, Z and n have the meaning given above are obtained if compounds of the formula (IIc)

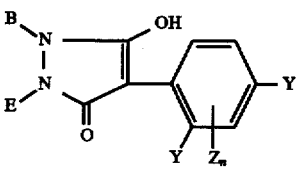
(IIc)

in which

B, E, X, Y, Z and n have the meaning given above are reacted with compounds of the formula (III)

G—L—M (III)

in which

L and M have the meaning given above
and

G represents a leaving group, such as halogen, sulphonylalkyl or sulphonylaryl, in the presence of a diluent and in the presence of a base.

Surprisingly, the novel substituted aryl keto-enolic heterocycles (Ia), (Ib) and (Ic) display good acaricidal, insecticidal and herbicidal properties.

The compounds according to the invention are defined in general by the formula (I).

X preferably represents $C_1$–$C_6$-alkyl, halogen or $C_1$–$C_6$-alkoxy.

Y preferably represents hydrogen, $C_1$–$C_6$-alkyl, halogen $C_1$–$C_6$-alkoxy or $C_1$–$C_3$-halogenoalkyl.

Z preferably represents $C_1$–$C_6$-alkyl, halogen or $C_1$–$C_6$-alkoxy.

n preferably represents a number from 0 to 3.

Het preferably represents a heterocyclic group from the series

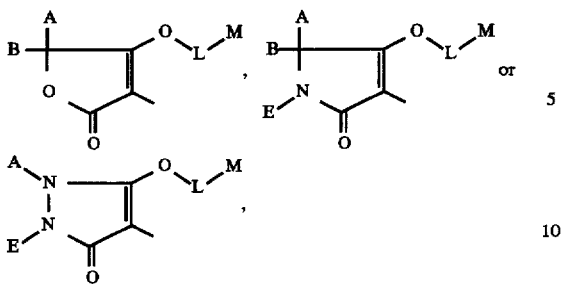

in which

A and B are identical or different and represent hydrogen or in each case optionally halogen-substituted straight-chain or branched $C_1$–$C_{12}$-alkyl, $C_3$–$C_8$-alkenyl, $C_1$–$C_{10}$-alkoxy-$C_2$–$C_8$-alkyl, $C_1$–$C_8$-polyalkoxy-$C_2$–$C_8$-alkyl, $C_1$–$C_{10}$-alkylthio-$C_2$–$C_8$-alkyl, cycloalkyl having 3 to 8 ring atoms, which can be interrupted by oxygen and/or sulphur, or phenyl, pyrimidyl, imidazolyl, pyrazolyl, triazolyl, indolyl, thiazolyl or phenyl-$C_1$–$C_6$-alkyl each of which is optionally substituted by halogen, $C_1$–$C_6$-alkyl, $C_1$–$C_6$-haloalkyl, $C_1$–$C_6$-alkoxy, $C_1$–$C_6$-halogenoalkoxy or nitro, or in which A and B, together with the carbon atom to which they are attached, form a saturated or unsaturated 3- to 8-membered ring which is optionally interrupted by oxygen and/or sulphur and is optionally substituted by halogen, $C_1$–$C_6$-alkyl, $C_1$–$C_6$ alkoxy, $C_1$–$C_4$-halogenoalkyl, $C_1$–$C_4$-halogenoalkoxy, $C_1$–$C_4$-alkylthio or phenyl which is optionally substituted by halogen, $C_1$–$C_6$-alkyl, $C_1$–$C_6$-alkoxy, E represents hydrogen or in each case optionally halogen-substituted straight-chain or branched $C_1$–$C_{12}$-alkyl, $C_3$–$C_8$-alkenyl, $C_1$–$C_{10}$-alkoxy-$C_2$–$C_8$-alkyl, $C_1$–$C_8$-polyalkoxy-$C_2$–$C_8$-alkyl, $C_1$–$C_{10}$-alkylthio-$C_2$–$C_8$-alkyl, cycloalkyl having 3 to 8 ring atoms, which can be interrupted by oxygen and/or sulphur, or phenyl, pyrimidyl, imidazolyl, pyrazolyl, triazolyl, indolyl, thiazolyl or phenyl-$C_1$–$C_6$-alkyl each of which is optionally substituted by halogen, $C_1$–$C_6$-alkyl, $C_1$–$C_6$-haloalkyl, $C_1$–$C_6$-alkoxy, $C_1$–$C_6$-halogenoalkoxy or nitro, or in which A and E, together with the atoms to which they are attached, form a saturated or unsaturated 3- to 8-membered ring which is optionally interrupted by oxygen and/or sulphur and is optionally substituted by halogen, $C_1$–$C_6$-alkyl, $C_1$–$C_6$ alkoxy, $C_1$–$C_4$-halogenoalkyl, $C_1$–$C_4$-halogenoalkoxy, $C_1$–$C_4$-alkylthio or phenyl which is optionally substituted by halogen, $C_1$–$C_6$-alkyl, $C_1$–$C_6$-alkoxy, or, if Het in formula (I) represents a pyrazolinone ring, A and E, together with the two nitrogen atoms of the pyrazoline ring, represent a group of the formulae 1 to 4 listed below

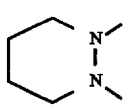 1

 2

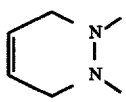 3

 4 which is optionally monosubstituted or polysubstituted by identical or different substituents consisting of $C_1$–$C_6$-alkyl, $C_1$–$C_6$-halogenoalkyl or halogen.

L preferably represents an alkanediyl group having 1 to 6 carbon atoms.

M preferably represents one of the following:

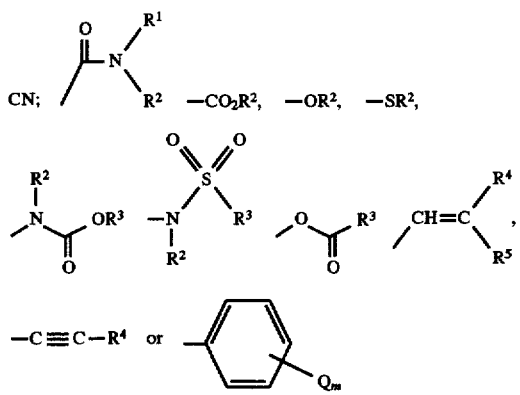

$R^1$ preferably represents hydrogen or $C_1$–$C_{12}$-alkyl.

$R^2$ preferably represents in each case optionally halogen-substituted $C_1$–$C_{12}$-alkyl, $C_3$–$C_8$-alkenyl, $C_3$–$C_8$-alkinyl, $C_3$–$C_8$-cycloalkyl, $C_1$–$C_8$-alkoxy-$C_2$–$C_8$-alkyl, $C_1$–$C_8$-alkylthio-$C_2$–$C_8$-alkyl or phenyl or benzyl each of which is optionally substituted by halogen, nitro, cyano, $C_1$–$C_6$-alkoxy, $C_1$–$C_6$ haloalkoxy, $C_1$–$C_6$-alkylthio, $C_1$–$C_6$-haloakylthio, $C_1$–$C_6$-alkyl or $C_1$–$C_6$-halogenoalkyl.

$R^3$ preferably represents optionally halogen-substituted $C_1$–$C_{12}$-alkyl, or represents phenyl or benzyl each of which is substituted by halogen, $C_1$–$C_6$-alkyl or $C_1$–$C_6$-alkoxy.

$R^4$ preferably represents hydrogen, halogen, optionally halogen-substituted $C_1$–$C_6$-alkyl or phenyl which is in each case substituted by halogen, $C_1$–$C_6$-alkyl or $C_1$–$C_6$-alkoxy, $C_1$–$C_4$-haloalkyl, $C_1$–$C_4$-haloalkoxy, cyano or nitro.

$R^5$ preferably represents hydrogen, halogen or optionally halogen-substituted $C_1$–$C_6$-alkyl.

Q preferably represents halogen, $C_1$–$C_6$-alkyl, $C_1$–$C_6$-alkoxy, $C_1$–$C_4$-haloalkyl, $C_1$–$C_4$-haloalkoxy, cyano or nitro.

m preferably represents a number 0, 1, 2 or 3.

X particularly preferably represents $C_1$–$C_6$-alkyl, fluorine, chlorine, bromine or $C_1$–$C_6$-alkoxy.

Y particularly preferably represents hydrogen, $C_1$–$C_6$-alkyl, fluorine, chlorine, bromine, $C_1$–$C_6$-alkoxy or $C_1$–$C_2$-halogenoalkyl.

Z particularly preferably represents $C_1$–$C_4$-alkyl, fluorine, chlorine, bromine or $C_1$–$C_4$-alkoxy.

n particularly preferably represents a number from 0 to 2.

Het particularly preferably represents a heterocyclic group from the series

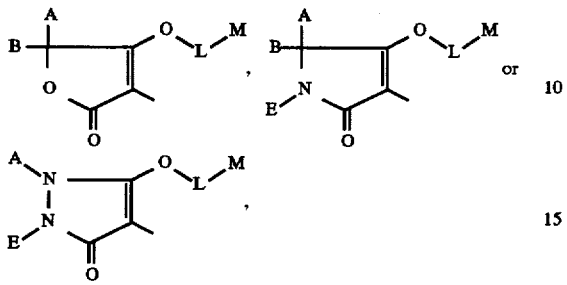

in which

A and B are identical or different and represent hydrogen, in each case optionally halogen-substituted straight-chain or branched $C_1$–$C_{10}$-alkyl, $C_3$–$C_6$-alkenyl, $C_1$–$C_8$-alkoxy-$C_2$–$C_6$-alkyl, $C_1$–$C_6$-polyalkoxy-$C_2$–$C_6$-alkyl, $C_1$–$C_8$-alkylthio-$C_2$–$C_6$-alkyl, cycloalkyl having 3 to 7 ring atoms, which can be interrupted by 1-2 oxygen and/or sulphur atoms, or phenyl, pyridinyl, imidazolyl, pyrazolyl, triazolyl, indolyl, thiazolyl or phenyl-$C_1$–$C_4$-alkyl each of which is optionally substituted by halogen, $C_1$–$C_4$-alkyl, $C_1$–$C_4$-haloalkyl, $C_1$–$C_4$-alkoxy, or nitro, or in which A and B, together with the carbon atom to which they are attached, form a saturated or unsaturated 3- to 8-membered ring which is optionally interrupted by oxygen and/or sulphur and is optionally substituted by halogen, $C_1$–$C_5$-alkyl, $C_1$–$C_5$ alkoxy, $C_1$–$C_3$-halogenoalkyl, $C_1$–$C_4$-halogenoalkoxy, $C_1$–$C_3$-alkylthio or phenyl which is optionally substituted by halogen, $C_1$–$C_4$-alkyl, $C_1$–$C_4$-alkoxy, E represents hydrogen or in each case optionally halogen-substituted straight-chain or branched $C_1$–$C_{10}$-alkyl, $C_3$–$C_6$-alkenyl, $C_1$–$C_8$-alkoxy-$C_2$–$C_6$-alkyl, $C_1$–$C_6$-polyalkoxy-$C_2$–$C_6$-alkyl, $C_1$–$C_8$-alkylthio-$C_2$–$C_6$-alkyl, cycloalkyl having 3 to 7 ring atoms, which can be interrupted by 1-2 oxygen and/or sulphur atoms, or phenyl, pyridinyl, imidazolyl, pyrazolyl, triazolyl, indolyl, thiazolyl or phenyl-$C_1$–$C_4$-alkyl each of which is optionally substituted by halogen, $C_1$–$C_4$-alkyl, $C_1$–$C_4$-halogenoalkyl, $C_1$–$C_4$-alkoxy or nitro, or in which A and E, together with the atoms to which they are attached, form a saturated or unsaturated 3- to 8-membered ring which is optionally interrupted by oxygen and/or sulphur and is optionally substituted by halogen, $C_1$–$C_5$-alkyl, $C_1$–$C_5$-alkoxy, $C_1$–$C_3$-halogenoalkyl, $C_1$–$C_4$-halogenoalkoxy, $C_1$–$C_3$-alkylthio or phenyl which is optionally substituted by halogen, $C_1$–$C_4$-alkyl, $C_1$–$C_4$-alkoxy, or, if Het in formula (I) represents a pyrazolinone ring, A and E, together with the two nitrogen atoms of the pyrazoline ring, represent a group of the formulae 1 or 2 listed below which is optionally monosubstituted or polysubstituted by identical or different substituents consisting of $C_1$–$C_4$-alkyl, $C_1$–$C_4$-halogenoalkyl, fluorine or chlorine,

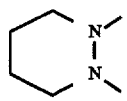

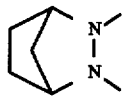

L particularly preferably represents an alkanediyl group having 1 to 4 carbon atoms.

M particularly preferably represents one of the following groups:

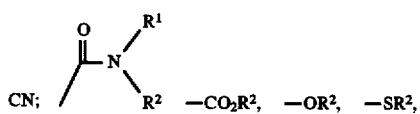

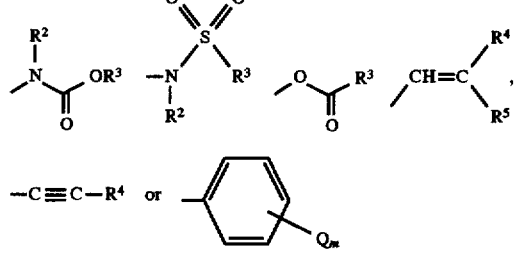

$R^1$ particularly preferably represents hydrogen or $C_1$–$C_{10}$-alkyl.

$R^2$ particularly preferably represents in each case optionally fluorine-, chlorine-, bromine-substituted $C_1$–$C_{10}$-alkyl, $C_3$–$C_6$-alkenyl, $C_3$–$C_6$-alkinyl, $C_3$–$C_8$-cycloalkyl, $C_1$–$C_6$-alkoxy-$C_2$–$C_6$-alkyl, $C_1$–$C_6$-alkylthio-$C_2$–$C_6$-alkyl, or phenyl or benzyl each of which is optionally substituted by fluorine, chlorine, bromine, nitro, cyano, $C_1$–$C_4$-alkylthio, $C_1$–$C_4$-alkoxy, $C_1$–$C_4$-halogenoalkoxy, $C_1$–$C_4$-halogenoalkylthio, $C_1$–$C_4$-alkyl or $C_1$–$C_4$-halogenoalkyl.

$R^3$ particularly preferably represents optionally fluorine-, chlorine-, bromine-substituted $C_1$–$C_{10}$-alkyl, or represents phenyl or benzyl each of which is substituted by fluorine, chlorine, $C_1$–$C_4$-alkyl or $C_1$–$C_4$-alkoxy.

$R^4$ particularly preferably represents hydrogen, fluorine, chlorine, bromine, optionally fluorine- or chlorine-substituted $C_1$–$C_5$-alkyl or phenyl which is substituted by fluorine, chlorine, bromine, $C_1$–$C_4$-alkyl or $C_1$–$C_4$-alkoxy, $C_1$–$C_2$-haloalkyl, $C_1$–$C_2$-haloalkoxy, cyano or nitro.

$R^5$ particularly preferably represents hydrogen, fluorine, chlorine, bromine or optionally fluorine- or chlorine-substituted $C_1$–$C_4$-alkyl.

Q particularly preferably represents fluorine, chlorine, bromine, $C_1$–$C_4$-alkyl, $C_1$–$C_4$-alkoxy, $C_1$–$C_2$-haloalkyl, $C_1$–$C_2$-haloalkoxy, cyano or nitro.

m particularly preferably represents a number 0, 1, or 2.

X very particularly preferably represents methyl, ethyl, propyl, isopropyl, fluorine, chlorine, bromine or methoxy.

Y very particularly preferably represents hydrogen, methyl, ethyl, propyl, isopropyl, butyl, isobutyl, tert-butyl, fluorine, chlorine, bromine, methoxy, ethoxy and trifluoromethyl.

Z very particularly preferably represents methyl, ethyl, propyl, isopropyl, butyl, isobutyl, tert-butyl, fluorine, chlorine, bromine, methoxy and ethoxy.

n very particularly preferably represents 1.

Het very particularly preferably represents a heterocyclic group from the series

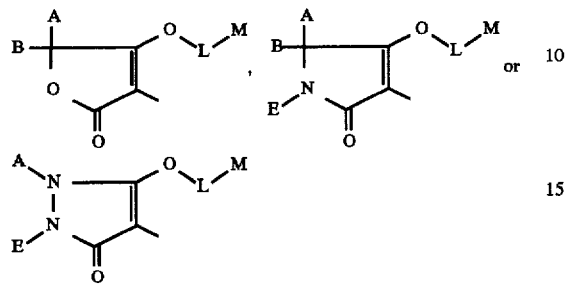

in which

A and B are identical or different and represent hydrogen, in each case optionally fluorine- or chlorine-substituted straight-chain or branched $C_1-C_8$-alkyl, $C_3-C_4$-alkenyl, $C_1-C_6$-alkoxy-$C_2-C_4$-alkyl, $C_1-C_4$-polyalkoxy-$C_2-C_4$-alkyl, $C_1-C_6$-alkylthio-$C_2-C_4$-alkyl, cycloalkyl having 3 to 6 ring atoms, which can be interrupted by 1-2 oxygen and/or sulphur atoms, or phenyl, pyridinyl, imidazolyl, indolyl or phenyl-$C_1-C_3$-alkyl each of which is optionally substituted by fluorine, chlorine, methyl, ethyl, propyl isopropyl, methoxy, ethoxy, trifluoromethyl or nitro, or in which A and B, together with the carbon atom to which they are attached, form a saturated or unsaturated 3- to 8-membered ring which is optionally interrupted by oxygen and/or sulphur and is optionally substituted by fluorine, chlorine, $C_1-C_4$-alkyl, $C_1-C_4$ alkoxy, trifluoromethyl, $C_1-C_2$-alkylthio or phenyl which is optionally substituted by fluorine, chlorine, methyl, methoxy, E represents hydrogen or in each case optionally fluorine- or chlorine-substituted straight-chain or branched $C_1-C_8$-alkyl, $C_3-C_4$-alkenyl, $C_1-C_6$-alkoxy-$C_2-C_4$-alkyl, $C_1-C_4$-polyalkoxy-$C_2-C_4$-alkyl, $C_1-C_6$-alkylthio-$C_2-C_4$-alkyl, cycloalkyl having 3 to 6 ring atoms, which can be interrupted by 1-2 oxygen and/or sulphur atoms, or represents phenyl, pyridinyl, imidazolyl, indolyl or phenyl-$C_1-C_3$-alkyl which is optionally substituted by fluorine, chlorine, methyl, ethyl, propyl, isopropyl, methoxy, ethoxy, trifluoromethyl or nitro, or in which A and E, together with the atoms to which they are attached, form a saturated or unsaturated 3- to 8-membered ring which is optionally interrupted by oxygen and/or sulphur and is optionally substituted by fluorine, chlorine, $C_1-C_4$-alkyl, $C_1-C_4$-alkoxy, trifluoromethyl, $C_1-C_2$-alkylthio or phenyl which is optionally substituted by fluorine, chlorine, methyl, methoxy, or, if Het in formula (I) represents a pyrazolinone ring, A and E, together with the two nitrogen atoms of the pyrazoline ring, represent a group of the formulae 1 or 2 listed below which is optionally monosubstituted to trisubstituted by identical or different substituents consisting of methyl, fluorine or chlorine,

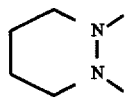

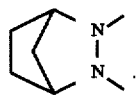

L very particularly preferably represents one of the following groups.

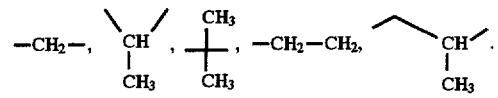

M very particularly preferably represents one of the following groups:

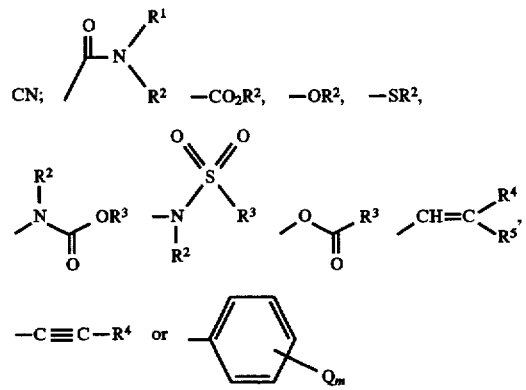

$R^1$ very particularly preferably represents hydrogen or $C_1-C_8$-alkyl.

$R^2$ very particularly preferably represents in each case optionally fluorine-, chlorine-, bromine-substituted $C_1-C_8$-alkyl, $C_3-C_4$-alkenyl, $C_3-C_4$-alkinyl, cyclopropyl, cyclopentyl, cyclohexyl, $C_1-C_6$-alkoxy-$C_2-C_4$-alkyl, $C_1-C_6$-alkylthio-$C_2-C_4$-alkyl, or represents phenyl or benzyl each of which is optionally substituted by fluorine, chlorine, bromine, nitro, cyano, methylthio, ethylthio, methoxy, ethoxy, trifluoromethylthio, trifluoromethoxy, methyl, ethyl, trifluoromethyl.

$R^3$ very particularly preferably represents in each case optionally fluorine-, chlorine-, bromine-substituted $C_1-C_8$-alkyl, or phenyl or benzyl which is substituted by fluorine, chlorine, $C_1-C_2$-alkyl or $C_1-C_2$-alkoxy.

$R^4$ very particularly preferably represents hydrogen, fluorine, chlorine, optionally fluorine- or chlorine-substituted $C_1-C_4$-alkyl, or phenyl which is substituted by fluorine, chlorine, methyl, ethyl, methoxy, ethoxy, trifluoromethyl, difluoromethoxy, trifluoromethoxy, cyano or nitro.

$R^5$ very particularly preferably represents hydrogen, fluorine, chlorine or optionally fluorine- or chlorine-substituted methyl, ethyl, propyl or isopropyl.

Q very particularly preferably represents fluorine, chlorine, methyl, ethyl, propyl, isopropyl, methoxy, ethoxy, propoxy, isopropoxy, trifluoromethyl, difluoromethoxy, trifluoromethoxy, cyano or nitro.

m very particularly preferably represents a number from 0 to 2.

In each of these sets of definitions the enantiomerically pure forms of compounds of the formula (I) are included.

The above-listed radical definitions and explanations, whether general or listed in ranges of preference, can be combined with one another as desired, i.e. including combinations between the respective ranges and ranges of preference. They apply to the end products and to the precursors and intermediates.

Preference is given in according with the invention to the compounds of the general formula (I) in which there is a combination of the definitions listed above as being preferred (preferably).

Particular preference is given in accordance with the invention to the compounds of a general formula (I) in which there is a combination of the definitions listed above as being particularly preferred.

Very particular preference is given in accordance with the invention to the compounds of the general formula (I) in which there is a combination of these definitions listed above as being very particularly preferred.

Using 3-(2,4-dichlorophenyl)-4-hydroxy-5-methyl-$\Delta^3$-furan-2-one and chloromethyl ethyl ether in accordance with process (A), the course of the process according to the invention can be illustrated by the following equation:

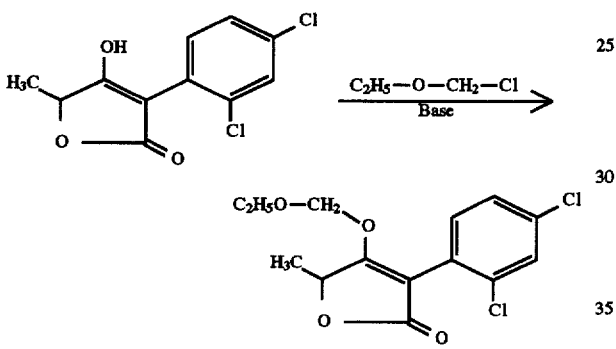

Using 3-(2,6-dichlorophenyl)-4-hydroxy-1-isopropyl-$\Delta^3$-pyrrolin-2-one and ethyl N-chloromethyl-N-methyl-carbamate in accordance with process (B), the course of the process according to the invention can be illustrated by the following equation.

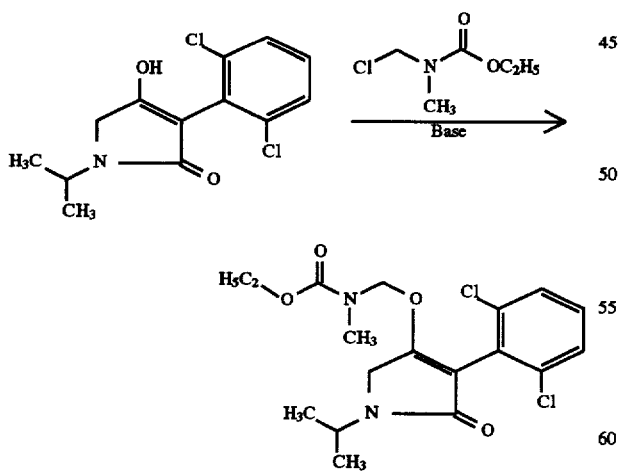

Using 3-(2,4,6-trimethylphenyl)-5-hydroxy-1,2-tetramethylene-$\Delta^4$-pyrazolin-3-one and chloromethyl phenyl ether in accordance with process (C), the process according to the invention can be illustrated by the following equation:

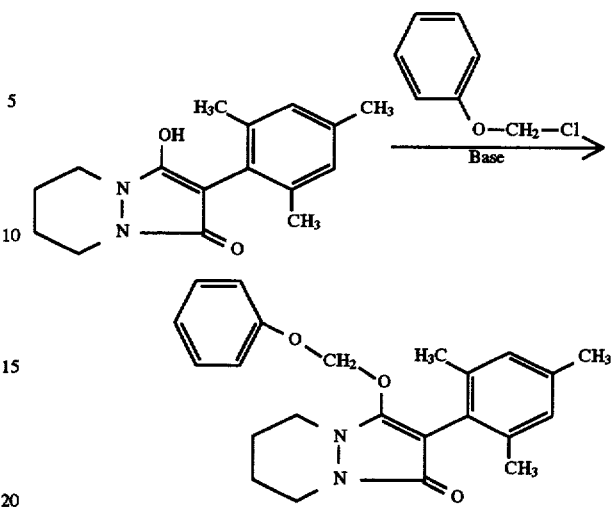

The compounds of the formula (IIa)

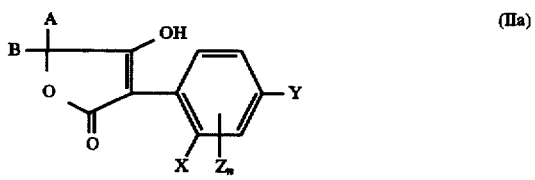

(IIa)

in which

A, X, Y, Z and n have the meaning given above, which are required as starting materials in the process (A), are known (EP 528 156).

The compounds of the formula (IIb)

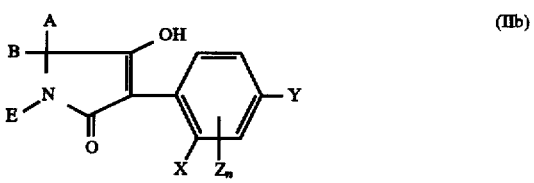

(IIb)

in which

A, B, E, X, Y, Z and n have the meaning given above, which are required as starting materials in the process (B), are known (cf. for example, EP 355 999, EP 377 893, EP 415 211, EP 442 073, EP 456 063, EP 497 127, EP 501 129).

The compounds of the formula (IIc)

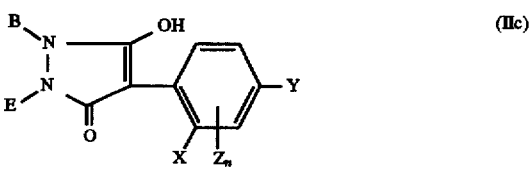

(IIc)

in which

E, B, X, Y, Z and n have the meaning given above, which are required as starting materials in the process (C), are known (cf. for example WO 92/16510 and EP 508 126).

The compounds of the formula (III) which are additionally required as starting compounds for carrying out the processes (A), (B) and (C) according to the invention are generally known compounds of organic chemistry.

Diluents which can be used for carrying out the processes (A), (B) and (C) according to the invention are all solvents which are inert with respect to these compounds. Preferred possibilities for use are hydrocarbons, such as benzine, benzene, toluene, xylene and tetralin; also halogenated hydrocarbons, such as methylene chloride, chloroform, carbon tetrachloride, chlorobenzene and o-dichlorobenzene; ethers, such as diethyl ether, tetrahydrofuran and dioxane; nitriles, such as acetonitrile or propionitrile; and also polar solvents which are inert with respect to the compounds of the formula (III), such as dimethyl sulphoxide, dimethylformamide, sulpholane or N-methylpyrrolidone.

Bases which can be employed in carrying out the processes (A), (B) and (C) according to the invention are all customary acid acceptors. Preferred possibilities for use are alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase transfer catalysts such as, for example, triethylbenzylammonium chloride, tetrabutylammonium bromide, Adogen 464*) or TDA 1***). Alkali metal and alkaline earth metal hydrides, such as sodium amide, sodium hydride and calcium hydride, and also alkali metal alcoholates as well, such as sodium methylate, sodium ethylate and potassium tertbutulate, can also be employed. In addition, tertiary amines, such as triethylamine, pyridine, DABCO, DBU, DBA, Hünig base and N,N-dimethylaniline.

*) Adogen 464=methyltrialkyl($C_8$-$C_{10}$)ammonium chloride
***) TDA1=tris-(methoxyethoxyethyl)-amine The reaction temperatures when carrying out the processes (A), (B) and (C) according to the invention can be varied within a relatively wide range. The processes are generally carried out at temperatures of between −20° C. and 180° C., preferably 0° C. and 130° C.

When carrying out the processes (A), (B) and (C) according to the invention, the reaction components (IIa) and (III) or (IIb) and (III) or (IIc) and (III) and the base are generally employed in approximately equimolar quantities. However, it is also possible to use one or other component in a relatively large excess (up to 3 mol).

The processes (A), (B) and (C) according to the invention are generally carried out under atmospheric pressure. The products are worked up by customary methods.

The active compounds are suitable for combating animal pests, preferably arthropods and nematodes; in particular insects and arachnida, encountered in agriculture, in forestry, in the protection of stored products and of materials, and in the hygiene field, and have good plant tolerance and they are active against normally sensitive and resistent species and against all or some stages of development. The abovementioned pests include:

From the order of the Isopoda, for example, *Oniscus asellus*, *Armadillidium vulgare* and *Porcellio scaber*.

From the order of the Diplopoda, for example, *Blaniulus guttulatus*.

From the order of the Chilopoda, for example, *Geophilus carpophagus* and *Scutigera spec.*

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis*, *Periplaneta americana*, *Leucophaea maderae*, *Blattella germanica*, *Acheta domesticus*, *Gryllotalpa* spp., *Locusta migratoria migratorioides*, *Melanoplus differentialis* and *Schistocerca gregaria*.

From the order of the Dermaptera, for example, *Forficula auricularia*.

From the order of the Isoptera, for example, Reticulitermes spp.

From the order of the Anoplura, for example, *Phylloxera vastatrix*, Pemphigus spp., *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Eurygaster spp., *Dysdercus intermedius*, *Piesma quadrata*, *Cimex lectularius*, *Rhodnius prolixus* and Triatoma spp.

From the order of the Homoptera, for example, *Aleurodes brassicae*, *Bemisia tabaci*, *Trialeurodes vaporariorum*, *Aphis gossypii*, *Brevicoryne brassicae*, *Cryptomyzus ribis*, *Doralis fabae*, *Doralis pomi*, *Eriosoma lanigerum*, *Hyalopterus arundinis*, *Macrosiphum avenae*, Myzus spp., *Phorodon humuli*, *Rhopalosiphum padi*, Empoasca spp., *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, Pseudococcus spp. and Psylla spp.

From the order of the Lepidoptera, for example, *Pectinophora gossypiella*, *Bupalus piniarius*, *Cheimatobia brumata*, *Lithocolletis blancardella*, *Hyponomeuta padella*, *Plutella maculipennis*, *Malacosoma neustria*, *Euproctis chrysorrhoea*, Lymantria spp. *Bucculatrix thurberiella*, *Phyllocnistis citrella*, Agrotis spp., Euxoa spp., Feltia spp., *Earias insulana*, Heliothis spp., *Laphygma exigua*, *Mamestra brassicae*, *Panolis flammea*, *Prodenia litura*, Spodoptera spp., *Trichoplusia ni*, *Carpocapsa pomonella*, Pieris spp., Chilo spp., *Pyrausta nubilalis*, *Ephestia kuehniella*, *Galleria mellonella*, *Tineola bisselliella*, *Tinea pellionella*, *Hofmannophila pseudospretella*, *Cacoecia podana*, *Capua reticulana*, *Choristoneura fumiferana*, *Clysia ambiguella*, *Homona magnanima* and *Tortrix viridana*.

From the order of the Coleoptera, for example, *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, Diabrotica spp., *Psylliodes chrysocephala*, *Epilachna varivestis*, Atomaria spp., *Oryzaephilus surinamensis*, Anthonomus spp., Sitophilus spp., *Otiorrhynchus sulcatus*, *Cosmopolites sordidus*, *Ceuthorrhynchus assimilis*, *Hypera postica*, Dermestes spp., Trogoderma spp., Anthrenus spp., Attagenus spp., Lyctus spp., *Meligethes aeneus*, Ptinus spp., *Niptus hololeucus*, *Gibbium psylloides*, Tribolium spp., *Tenebrio molitor*, Agriotes spp., Conoderus spp., *Melolontha melolontha*, *Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonycus spp., Tetranychus spp.

The active compounds according to the invention are distinguished by a high insecticidal and acaricidal activity.

They can be employed with particular success in combatting phytopathogenic mites, for example against the common spider mite or two-spotted spider mite (*Tetranychus urticae*) or against the fruit tree red spider mite (*Panonychus ulmi*).

The active compounds according to the invention additionally display a fungicidal activity, an activity against *Pyricularia oryzae* and are active against Oomycetes such as, for example, Phythophtora and Plasmopara).

The active compounds according to the invention can be used as defoliants, desiccants, agents for destroying broad-leaved plants and, especially, as weed-killers. By weeds, in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The compounds of the formula (I) according to the invention are very suitable for the selective pre-emergence combatting of monocotyledon weeds in dicotyledon cultures. They can be employed, for example, in soya bean with great success for the combatting of grass weeds.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foamforming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in their formulations, can also be used as mixtures with known herbicides, finished formulations or tank mixes being possible.

Possible components for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxyphenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulfonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl thifensulfuron-methyl, triasulfuron and tribenuron-methyl; thiolcarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The insecticides include, for example, phosphates, carbamates, carboxylic esters, chlorinated hydrocarbons, phenolic ureas, substances produced by microorganisms, and others. The following compounds may be mentioned:

Acrinathrin, alphamethrin, betacyfluthrin, bifenthrin, brofenprox, cis-resmethrin, clocythrin, cycloprothrin, cyfluthrin, cyhalothrin, cypermethrin, deltamethrin, esfenvalerate, etofenprox, fenpropathrin, fenvalerate, flucythrinate, fluvalinate, lambda-cyhalothrin, permethrin, pyresmethrin, pyrethrum, silafluofen, tralomethrin zeta-methrin, alanycarb, bendiocarb, benfuracarb, bufencarb, butocarboxim carbaryl, cartap, ethiofencarb, fenobucarb, fenoxycarb, isoprocarb, methiocarb, methomyl, metolcarb, oxamyl, pirimicarb, promecarb, propoxur, terbam thiodicarb, thiofanox, trimethacarb, XMC, xylylcarb, acephate, azinphos A, azinphos M, bromophos A cadusafos, carbophenothion, chlorfenvinphos, chlormephos, chlorpyrifos, chlorpyrifos M, cyanophos, demeton M, demetons-methyl, demeton S, diazinon, dichlorvos, dicliphos, dichlorfenthion, dicrotophos, dimethoate, dimethylvinphos, dioxathion, disulfoton, edifenphos, ethion, etrimphos, fenitrothion, fenthion, fonophos, formothion, heptenophos, iprobenfos, isazophos, isoxathion, phorate, malathion, mecarbam, mervinphos, mesulfenphos, methacrifos, methamidophos, naled, omethoate, oxydemeton M, oxydeprofos, parathion A, parathion M, phenthoate, phorate, phosalone, phosmet, phosphamdom, phoxim, pirimiphos A, pirimiphos M, propaphos, prothiophos, prothoate, pyraclophos, pyridaphenthion, quinalphos, salithion, sebufos, sulfotep, sulprofos, tetrachlorvinphos, temephos, thiomethon, thionazin, trichlorfon, triazophos, vamidothion, buprofezin, chlorfluazuron, diflubenzuron, flucycloxuron, flufenoxuron, hexaflumuron, pyriproxifen, tebufenozide, teflubenzuron, triflumoron, imidacloprid, nitenpyram N-[(6-chloro-3-pyridinyl)methyl]-B'-cyano-N-methyl-ethanimideamide (NI-25), abamectin, amitrazin, avermectin, azadirachtin, bensultap, Bacillus thuringiensis, cyromazine, diafenthiuron, emamectin, ethofenprox, fenpyrad, fipronil, flufenprox, lufenuron, metaldehyde, milbemectin, pymetrozine, tebufenpyrad, triazuron, aldicarb, bendiocarb, benfuracarb, carbofuran, carbosulfan, chlorethoxyfos, cloethocarb, disulfoton, ethophrophos, etrimphos, fenamiphos, fipronil, fonofos, fosthiazate, furathiocarb, HCH, isazophos, isofenphos, methiocarb, monocrotophos, nitenpyram, oxamyl, phorate, phoxim, prothiofos, pyrachlofos, sebufos, silafluofen, tebupirimphos, tefluthrin, terbufos, thiodicarb, thiafenox, azocyclotin, butylpyridaben, clofentezine, cyhexatin, diafenthiuron, diethion, emamectin, fenzaquin, fenbutatin oxide, fenothiocarb, fenpropathrin, fenpyrad, fenpyroximate, fluazinam, fluazuron, flucycloxuron, flufenoxuron, fluvalinate, fubfenprox, hexythiazox, ivemectin, methidathion, monocrotophos, moxidectin, naled, phosalone, profenofos, pyraclofos, pyridaben, pyrimidifen, tebufenpyrad, thuringiensin, triarathene and 4-bromo-2-(4-chlorophenyl)-1-(ethoxymethyl)-5-(trifluoromethyl)-1H-pyrrole-3-carbonitrile (AC 303630).

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the following examples.

PREPARATION EXAMPLES

Example Ia-1

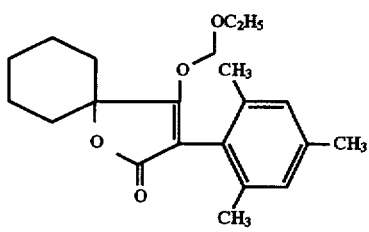

1.47 g (15.5 mmol) of chloromethyl ethyl ether in 15 ml of absolute dichloromethane are added dropwise under a nitrogen atmosphere from 0° C. to 10° C. to 4.3 g (15 mmol) of 3-(2,4,6-trimethylphenyl)-4-hydroxy-5,5-pentamethylene-$\Delta^3$-dihydrofuran-2-one in 60 ml of absolute dichloromethane, 1.67 g (16.5 mmol) of triethylamine and a spatula tip of DMAP. The reaction mixture is stirred at room temperature for about 20 hours, then washed in succession with 10% strength citric acid, sodium hydrogen carbonate solution and sodium chloride solution, the organic phase is dried over sodium sulphate, and the solvent is stripped off. The crude product is purified further on a silica gel column (eluent:chloroform/ethyl acetate 3:1).

2.47 g (53% of theory) are obtained of 3-(2,4,6-trimethylphenyl)-4-ethoxymethyloxy)-5,5-pentamethylene-$\Delta^3$-dihydrofuran-2-one, of melting point m.p. 102° C.

In analogy to Example I, the compound of the following preparation examples of the formula (Ita) were synthesized

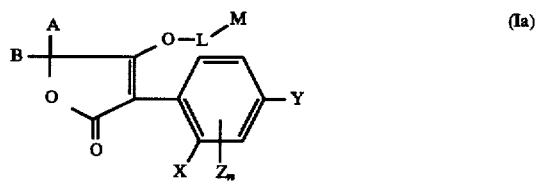
(Ia)

TABLE 1

| Ex. No | A B | L | X | Y | $Z_n$ | M | Physical constants |
|---|---|---|---|---|---|---|---|
| Ia-2 | —(CH$_2$)$_5$— | —CH$_2$— | CH$_3$ | CH$_3$ | 6-CH$_3$ | —N(C$_2$H$_5$)(CO$_2$CH$_3$) | oil |
| Ia-3 | —(CH$_2$)$_5$— | —CH$_2$— | Cl | Cl | H | —O—CH$_2$—C$_6$H$_5$ | m.p.: 106° C. |
| Ia-4 | —(CH$_2$)$_5$— | —CH$_2$— | Cl | Cl | H | —OC$_2$H$_5$ | m.p.: 67° C. |
| Ia-5 | —(CH$_2$)$_5$— | —CH$_2$— | Cl | Cl | H | —OC$_8$H$_{17}$-n | m.p.: 62° C. |
| Ia-6 | —(CH$_2$)$_5$— | —CH$_2$— | Cl | Cl | H | —O—C$_6$H$_4$—Cl | m.p.: 57° C. |
| Ia-7 | —(CH$_2$)$_5$— | —CH$_2$— | Cl | Cl | H | —O—CO—C$_4$H$_9$-t | m.p.: 96° C. |
| Ia-8 | —(CH$_2$)$_5$— | —CH$_2$— | Cl | Cl | H | —O—C$_2$H$_4$—OCH$_3$ | m.p.: 67° C. |
| Ia-9 | —(CH$_2$)$_5$— | —CH$_2$— | CH$_3$ | CH$_3$ | 6-CH$_3$ | —OC$_3$H$_7$-i | m.p.: 81–82° C. |
| Ia-10 | —(CH$_2$)$_5$— | —CH$_2$— | CH$_3$ | CH$_3$ | 6-CH$_3$ | —O—CO—C$_4$H$_9$-t | m.p.: 98–99° C. |
| Ia-11 | —(CH$_2$)$_5$— | —CH$_2$— | CH$_3$ | CH$_3$ | 6-CH$_3$ | —OC$_4$H$_9$-i | oil |
| Ia-12 | —(CH$_2$)$_5$— | —CH$_2$— | CH$_3$ | CH$_3$ | 6-CH$_3$ | —N(C$_3$H$_7$-n)(CO$_2$C$_2$H$_5$) | oil |
| Ia-13 | —(CH$_2$)$_5$— | —CH$_2$— | CH$_3$ | CH$_3$ | 6-CH$_3$ | —N(C$_6$H$_{11}$)(CO$_2$C$_2$H$_5$) | oil |
| Ia-14 | —(CH$_2$)$_5$— | —CH$_2$— | CH$_3$ | CH$_3$ | 6-CH$_3$ | —N(CH$_3$)(CO$_2$CH$_2$—C$_6$H$_4$—Cl) | oil |
| Ia-15 | —(CH$_2$)$_5$— | —CH$_2$— | CH$_3$ | CH$_3$ | 6-CH$_3$ | —N(C$_4$H$_9$-t)(CO$_2$CH$_3$) | oil |

TABLE 1-continued

| Ex. No | A B | L | X | Y | $Z_n$ | M | Physical constants |
|---|---|---|---|---|---|---|---|
| Ia-16 | —(CH$_2$)$_5$— | —CH$_2$— | Cl | Cl | H | 4-Cl-C$_6$H$_4$-S— | m.p.: 65° C. |
| Ia-17 | —(CH$_2$)$_5$— | —CH$_2$— | Cl | Cl | H | —SCH$_3$ | m.p.: 120° C. |
| Ia-18 | —(CH$_2$)$_5$— | —CH$_2$— | Cl | Cl | H | —CN | m.p.: 158° C. |
| Ia-19 | —(CH$_2$)$_5$— | —CH$_2$— | Cl | Cl | H | —CO—C$_4$H$_9$-t | m.p.: 128° C. |
| Ia-20 | —(CH$_2$)$_5$— | —CH$_2$— | Cl | Cl | H | —CO—OCH$_3$ | m.p.: 127° C. |
| Ia-21 | —(CH$_2$)$_5$— | —CH$_2$— | Cl | Cl | H | —CO—OC$_4$H$_9$-t | M.P.: 126° C. |
| Ia-22 | —(CH$_2$)$_5$— | —CH$_2$— | Cl | H | 6-F | —CN | m.p.: 163° C. |
| Ia-23 | —(CH$_2$)$_5$— | —CH$_2$— | CH$_3$ | CH$_3$ | 6-CH$_3$ | —OCH$_2$—C≡CH | m.p.: 243° C. |
| Ia-24 | —(CH$_2$)$_5$— | —CH$_2$— | CH$_3$ | CH$_3$ | 6-CH$_3$ | —N(SO$_2$CH$_3$)—C$_6$H$_5$ | m.p.: 172–173° C. |
| Ia-25 | —(CH$_2$)$_5$— | —CH$_2$— | CH$_3$ | CH$_3$ | 6-CH$_3$ | —N(CH$_3$)—SO$_2$—C$_6$H$_5$ | m.p.: 145° C.–146 |
| Ia-26 | —(CH$_2$)$_2$—CH(CH$_3$)—(CH$_2$)$_2$— | —CH$_2$— | CH$_3$ | CH$_3$ | 6-CH$_3$ | —OC$_2$H$_5$ | oil |
| Ia-27 | —(CH$_2$)$_2$—CH(CH$_3$)—(CH$_2$)$_2$— | —CH$_2$— | CH$_3$ | CH$_3$ | 6-CH$_3$ | —N(C$_2$H$_5$)—CO$_2$CH$_3$ | oil |
| Ia-28 | —(CH$_2$)$_2$—CH(CH$_3$)—(CH$_2$)$_2$— | —CH$_2$— | CH$_3$ | CH$_3$ | 6-CH$_3$ | —N(CH$_3$)—SO$_2$CH$_3$ | m.p.: 145–147° C. |
| Ia-29 | —(CH$_2$)$_5$— | —CH$_2$— | CH$_3$ | CH$_3$ | 6-CH$_3$ | —S—CH$_3$ | m.p.: 125–127° C. |
| Ia-30 | —(CH$_2$)$_5$— | —CH$_2$— | CH$_3$ | CH$_3$ | 6-CH$_3$ | —N(CO$_2$CH$_3$)—(2-CH$_3$-C$_6$H$_4$) | m.p.: 156–157° C. |
| Ia-31 | —(CH$_2$)$_2$—CH(CH$_3$)—(CH$_2$)$_2$— | —CH$_2$— | CH$_3$ | CH$_3$ | 6-CH$_3$ | —N(CO$_2$CH$_3$)—(2-CH$_3$-C$_6$H$_4$) | oil |
| Ia-32 | —(CH$_2$)$_5$— | —CH$_2$— | CH$_3$ | CH$_3$ | 6-CH$_3$ | CH=CH$_2$ | m.p.: 89–91° C. |

In analogy to Example Ia-1, the Preparation Example Ib-1 is also obtained:

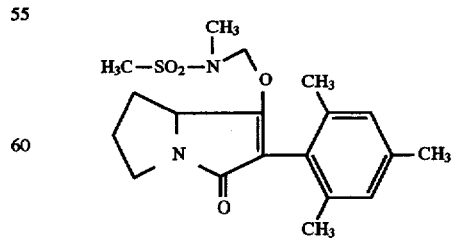

(Ib-1)

$^1$H-NMR (200 1MHz, CDCl$_3$): 2.12, 2.2, 2.26 (3s, 9H, Ar-C<u>H</u>$_3$), 3.88 (s, 3H, SO$_2$, C<u>H</u>$_3$), 3.92 (s, 3H, N-C<u>H</u>$_3$), 3.25, 3.62 (m, 2H, N-C<u>H</u>$_2$), 4.21 (dd, 1H, C<u>H</u>-N) 4.72 (ABq, 2H, O-C<u>H</u>$_2$N), 6.89 (s, 2H, Ar-<u>H</u>).

In analogy to Example Ia-1, the preparation example of formula (Ic-1) is also obtained, melting point m.p. 207° C.

Example Ic-1

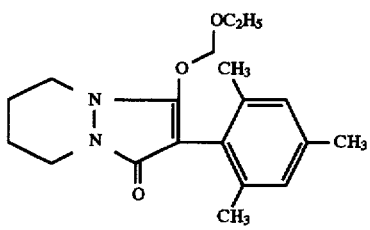

(Ic-1)

USE EXAMPLES

In the following use examples, the compound listed below was employed as comparison substance:

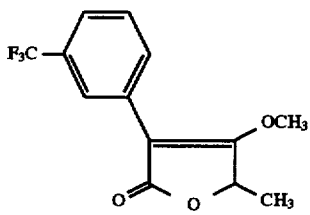

(A)

4-Methoxy-3-(3-trifluoromethylphenyl)-5-methyl-5H-furan-2-one (known from DE 39 31 773, Example 6).

Example A

Panonychus test

| Solvent: | 3 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with emulsifier containing water to the desired concentration.

About 30 cm high plum trees (*Prunus domestica*) which are heavily infested with all development stages of the fruit tree red spider mite (*Panonychus ulmi*) are sprayed with a preparation of the active compound of the desired concentration.

After the desired time, the action in % is determined. 100% means that all the spider mites have been killed; 0% means that none of the spider mites have been killed.

In this test, for example, the compounds of Preparation Examples Ia-1, Ia-2, Ia-5 and Ia-7 at an active compound concentration, used by way of example, of 0.02% brought about a destruction of 100% after 7 days.

Example B

Tetranychus test (OP resistent)

| Solvent: | 3 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are infested with all development stages of the of the common or two-spotted spider mite (*Tetranychus urticae*) are treated by being dipped into the preparation of the active compound of the desired concentration.

After the desired time, the destruction in % is determined. 100% means that all the spider mites have been killed; 0% means that none of the spider mites have been killed.

In this test, for example, the compounds of Preparation Examples Ia-1, Ia-2, Ia-5 and Ia-7 at an active compound concentration, used by way of example, of 0.02% brought about a destruction of at least 98% after 7 days.

Example C

Pre-emergence test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

In this test, for example, the compounds according to Preparation Example (Ia-1) and (Ia-2) display a very strong action against weeds while in some cases being very well tolerated by crop plants such as, for example, wheat and soya bean. At an application rate, used by way of example, of 1000 g/ha, Alopecurus, Cynodon, Digitaria, Lolium and Setaria for example, are at least 90% affected.

Example D

Phaedon larvae test

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*) for as long as the leaves are still moist.

After the desired time, the destruction in % is determined. 100% means that all the beetle larvae have been killed; 0% means that none of the beetle larvae have been killed.

In this test, for example, the compounds of Preparation Examples Ia-9, Ia-12, Ia-13 Ia-14, Ia-15, Ib-1 and Ic-1 at an active compound concentration, used by way of example, of 0.01% brought about a destruction of 100% after 7 days, whereas the known compound (A) brought about no destruction.

Example E

Plutella test

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of active compound of the desired concentration and are infested with caterpillars of the diamond-back moth (Plutella maculipennis) for as long as the leaves are still moist.

After the desired time, the destruction in % is determined. 100% means that all the caterpillars have been killed; 0% means that none of the caterpillars have been killed.

In this test, for example, the compounds of Preparation Examples Ia-14 and Ia-27, at an active compound concentration, used by way of example, of 0.01% brought about a destruction of 100% after 3 days, whereas the known compound (A) brought about no destruction.

Example F

Nephotettix test

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Rice seedlings (Oryza saliva) are treated by being dipped into the preparation of active compound of the desired concentration and are populated with the rice green leafhopper (Nephotettix cincticeps) for as long as the seedlings are still damp.

In this test, for example, the compounds of Preparation Examples Ia-1, Ia-3, Ia-9, Ia-12, Ia-13, Ia-15, Ia-25, Ia-26, Ia-27, Ia-28, Ia-31, Ib-1 and Ic-1 at an active compound concentration, used by way of example, of 0.01% brought about a destruction of 100% after 6 days, whereas the known compound (A) brought about no destruction.

Example G

Myzus test

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) which are heavily infested with the peach aphid are treated by being dipped into the preparation of active compound of the desired concentration.

After the desired time, the action is determined. 100% means that all the aphids have been killed; 0% means that none of the aphids have been killed.

In this test, for example, the compounds of Preparation Examples Ia-1, Ia-28 and Ia-31 at an active compound concentration, used by way of example, of 0.1% brought about a destruction of 100% after 6 days, whereas the known compound (A) brought about no destruction.

We claim:

1. A substituted aryl keto-enolic heterocycle of the formula $$\text{Het}\diagdown\diagup\text{Z}_n$$
$$X-\text{(ring)}$$
$$\diagdown\text{Y}$$

(I)

in which

X represents alkyl, halogen or alkoxy,

Y represents hydrogen, alkyl, halogen, alkoxy or halogenoalkyl,

Z represents alkyl, halogen or alkoxy, n represents a number 0, 1, 2 or 3,

Het represents a heterocyclic group selected from the group consisting of $$\begin{array}{c}A\\B\end{array}\diagdown\diagup\begin{array}{c}O\diagdown L\diagup M\\\\O\end{array}, \quad \begin{array}{c}A\\B\end{array}\diagdown\diagup\begin{array}{c}O\diagdown L\diagup M\\N\\E\diagdown\\O\end{array} \text{ or}$$

$$\begin{array}{c}A\diagdown N\\|\\N\\E\diagdown\end{array}\diagup\begin{array}{c}O\diagdown L\diagup M\\\\O\end{array}$$

A and B can be identical or different and represent hydrogen, in each case optionally halogen-substituted alkyl, alkenyl, alkoxyalkyl, alkylthioalkyl, cycloalkyl which is optionally interrupted by at least one heteroatom, or aryl, aralkyl or hetaryl each of which is optionally substituted by halogen, alkyl, halogenoalkyl, alkoxy, halogenoalkoxy or nitro, A and B, together with the carbon atom to which they are attached, form a saturated or unsaturated ring which is optionally interrupted by at least one heteroatom and is optionally substituted, E represents hydrogen, in each case optionally halogen-substituted alkyl, alkenyl, alkoxyalkyl, alkylthioalkyl, cycloalkyl which is optionally interrupted by at least one heteroatom, or aryl, aralkyl or hetaryl each of which is optionally substituted by halogen, alkyl, halogenoalkyl, alkoxy, halogenoalkoxy or nitro, or in which A and E, together with the atoms to which they are attached, form a saturated or unsaturated monocyclic, bicyclic or tricyclic ring system which is optionally interrupted by at least one heteroatom and is optionally substituted, L represents an alkanediyl group, M represents one of the following groups:

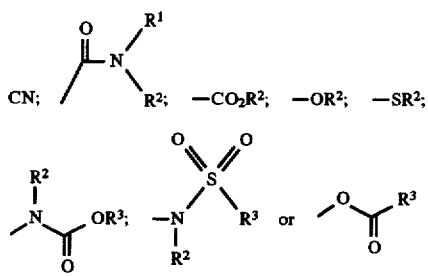

in which

R¹ represents hydrogen or alkyl,

R² represents in each case optionally substituted alkyl, alkenyl, alkinyl, cycloalkyl, alkoxyalkyl, alkylthioalkyl, aryl or aralkyl, R³ represents optionally substituted alkyl, aryl or aralkyl, or the enantiomerically pure forms thereof.

2. A compound according to claim 1, in which

X represents $C_1-C_6$-alkyl, halogen or $C_1-C_6$-alkoxy,

Y represents hydrogen, $C_1-C_6$-alkyl, halogen $C_1-C_6$-alkoxy or $C_1-C_3$-halogenoalkyl, Z represents $C_1-C_6$-alkyl, halogen or $C_1-C_6$-alkoxy, n represents a number from 0 to 3, Het represents a heterocyclic group selected from the group consisting of

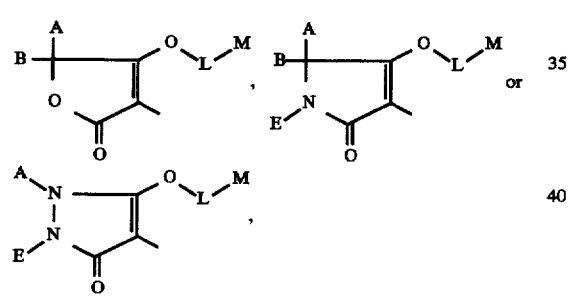

in which

A and B are identical or different and represent hydrogen or in each case optionally halogen-substituted straight-chain or branched $C_1-C_{12}$-alkyl, $C_3-C_8$-alkenyl, $C_1-C_{10}$ -alkoxy-$C_2-C_8$-alkyl, $C_1-C_8$ -polyalkoxy-$C_2-C_8$-alkyl, $C_1-C_{10}$-alkylthio-$C_2-C_8$-alkyl, cycloalkyl having 3 to 8 ring atoms, which can be interrupted by oxygen and/or sulphur, or phenyl, pyrimidyl, imidazolyl, pyrazolyl, triazolyl, indolyl, thiazolyl or phenyl-$C_1-C_6$-alkyl each of which is optionally substituted by halogen, $C_1-C_6$-alkyl, $C_1-C_6$-haloalkyl, $C_1-C_6$-alkoxy, $C_1-C_6$-halogenoalkoxy or nitro, or in which A and B, together with the carbon atom to which they are attached, form a saturated or unsaturated 3- to 8-membered ring which is optionally interrupted by oxygen and/or sulphur and is optionally substituted by halogen, $C_1-C_6$-alkyl, $C_1-C_6$ alkoxy, $C_1-C_4$-halogenoalkyl, $C_1-C_4$-halogenoalkoxy, $C_1-C_4$-alkylthio or phenyl which is optionally substituted by halogen, $C_1-C_6$-alkyl, $C_1-C_6$-alkoxy, E represents hydrogen or in each case optionally halogen-substituted straight-chain or branched $C_1-C_{12}$-alkyl, $C_3-C_8$-alkenyl, $C_1-C_{10}$-alkoxy-$C_2-C_8$-alkyl, $C_1-C_8$-polyalkoxy-$C_2-C_8$-alkyl, $C_1-C_{10}$-alkylthio-$C_2-C_8$-alkyl, cycloalkyl having 3 to 8 ring atoms, which can be interrupted by oxygen and/or sulphur, or phenyl, pyrimidyl, imidazolyl, pyrazolyl, triazolyl, indolyl, thiazolyl or phenyl-$C_1-C_6$-alkyl each of which is optionally substituted by halogen, $C_1-C_6$-alkyl, $C_1-C_6$-haloalkyl, $C_1-C_6$-alkoxy, $C_1-C_6$-halogenoalkoxy or nitro, or in which A and E, together with the atoms to which they are attached, form a saturated or unsaturated 3- to 8-membered ring which is optionally interrupted by oxygen and/or sulphur and is optionally substituted by halogen, $C_1-C_6$-alkyl, $C_1-C_6$ alkoxy, $C_1-C_4$-halogenoalkyl, $C_1-C_4$-halogenoalkoxy, $C_1-C_4$-alkylthio or phenyl which is optionally substituted by halogen, $C_1-C_6$-alkyl, $C_1-C_6$-alkoxy, or, if Het in formula (I) represents a pyrazolinone ring, A and E, together with two nitrogen atoms of the pyrazoline ring, represent a group of the formulae 1 to 4 listed below

which is optionally monosubstituted or polysubstituted by identical or different substituents consisting of $C_1-C_6$-alkyl, $C_1-C_6$-halogenoalkyl or halogen, L represents an alkanediyl group having 1 to 6 carbon atoms, M represents one of the following:

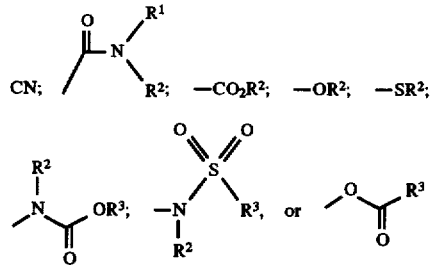

R¹ represents hydrogen or $C_1-C_{12}$-alkyl,

R² represents in each case optionally halogen-substituted $C_1-C_{12}$-alkyl, $C_3-C_8$-alkenyl, $C_3-C_8$-alkinyl, $C_3-C_8$-cycloalkyl, $C_1-C_8$-alkoxy-$C_2-C_8$-alkyl, $C_1-C_8$-alkylthio-$C_2-C_8$-alkyl or phenyl or benzyl each of which is optionally substituted by halogen, nitro, cyano, $C_1-C_6$-alkoxy, $C_1-C_6$-haloalkylthio, $C_1-C_6$-alkyl or $C_1-C_6$-halogenoalkyl, $R^3$ represents optionally halogen-substituted $C_1-C_{12}$-alkyl, or represents phenyl or benzyl each of which is substituted by halogen, $C_1-C_6$-alkyl or $C_1-C_6$-alkoxy, or the enantiomerically pure forms thereof.

3. A compound according to claim 1, in which

X represents $C_1-C_6$-alkyl, fluorine, chlorine, bromine or $C_1-C_6$-alkoxy,

Y represents hydrogen, $C_1-C_6$-alkyl, fluorine, chlorine, bromine, $C_1-C_6$-alkoxy or $C_1-C_2$-halogenoalkyl, Z represents $C_1-C_4$-alkyl, fluorine, chlorine, bromine or $C_1-C_4$-alkoxy, n represents a number from 0 to 2, Het represents a heterocyclic group selected from the group consisting of

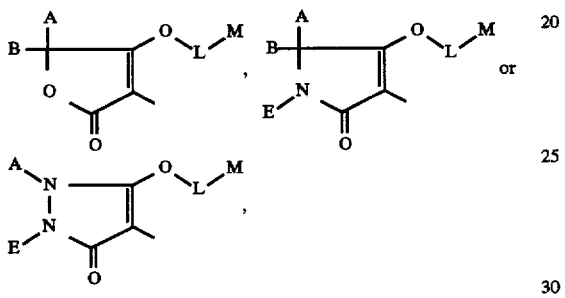

in which

A and B are identical or different and represent hydrogen, in each case optionally halogen-substituted straight-chain or branched $C_1-C_{10}$-alkyl, $C_3-C_6$-alkenyl, $C_1-C_8$-alkoxy-$C_2-C_6$-alkyl, $C_1-C_6$-polyalkoxy-$C_2-C_6$-alkyl, $C_1-C_8$-alkylthio-$C_2-C_6$-alkyl, cycloalkyl having 3 to 7 ring atoms, which can be interrupted by 1-2 oxygen and/or sulphur atoms, or phenyl, pyridinyl, imidazolyl, pyrazolyl, triazolyl, indolyl, thiazolyl or phenyl-$C_1-C_4$-alkyl each of which is optionally substituted by halogen, $C_1-C_4$-alkyl, $C_1-C_4$-haloalkyl, $C_1-C_4$-alkoxy, or nitro, or in which A and B, together with the carbon atom to which they are attached, form a saturated or unsaturated 3- to 8-membered ring which is optionally interrupted by oxygen and/or sulphur and is optionally substituted by halogen, $C_1-C_5$-alkyl, $C_1-C_5$-alkoxy, $C_1-C_3$-halogenoalkyl, $C_1-C_4$-halogenoalkoxy, $C_1-C_3$-alkylthio or phenyl which is optionally substituted by halogen, $C_1-C_4$-alkyl, $C_1-C_4$-alkoxy, E represents hydrogen or in each case optionally halogen-substituted straight-chain or branched $C_1-C_{10}$-alkyl, $C_3-C_6$-alkenyl, $C_1C_8$-alkoxy-$C_2-C_6$-alkyl, $C_1-C_6$-polyalkoxy-$C_2-C_6$-alkyl, $C_1$ $_{-C8}$-alkylthio-$C_2-C_6$-alkyl, cycloalkyl having 3 to 7 ring atoms, which can be interrupted by 1-2 oxygen and/or sulphur atoms, or phenyl, pyridinyl, imidazolyl, pyrazolyl, triazolyl, indolyl, thiazolyl or phenyl-$C_1-C_4$-alkyl each of which is optionally substituted by halogen, $C_1-C_4$-alkyl, $C_1-C_4$-halogenoalkyl, $C_1-C_4$-alkoxy or nitro, or in which A and E, together with the atoms to which they are attached, form a saturated or unsaturated 3- to 8-membered ring which is optionally interrupted by oxygen and/or sulphur and is optionally substituted by halogen, $C_1-C_5$-alkyl, $C_1-C_5$-alkoxy, $C_1-C_3$-halogenoalkyl, $C_1-C_4$- halogenoalkoxy, $C_1-C_3$-alkylthio or phenyl which is optionally substituted by halogen, $C_1-C_4$-alkyl, $C_1-C_4$-alkoxy, or, if Het in formula (I) represents a pyrazolinone ring, A and E, together with the two nitrogen atoms of the pyrazoline ring, represent a group of the formulae 1 or 2 listed below which is optionally monosubstituted or polysubstituted by identical or different substituents consisting of $C_1-C_4$-alkyl, $C_1-C_4$-halogenoalkyl, fluorine or chlorine,

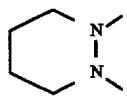 1

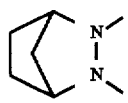 2

L represents an alkanediyl group having 1 to 4 carbon atoms,

M represents one of the following groups:

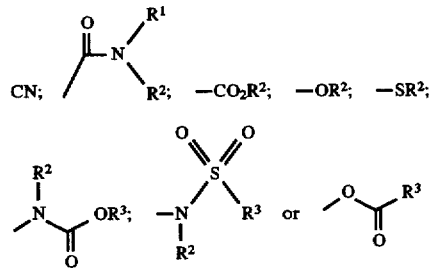

$R^1$ represents hydrogen or $C_1-C_{10}$-alkyl, $R^2$ represents in each case optionally fluorine-, chlorine-, bromine-substituted $C_1-C_{10}$-alkyl, $C_3-C_6$-alkenyl, $C_3-C_6$-alkinyl, $C_3-C_8$-cycloalkyl, $C_1-C_6$-alkoxy-$C_2-C_6$-alkyl, $C_1-C_6$-alkylthio-$C_2-C_6$-alkyl, or phenyl or benzyl each of which is optionally substituted by fluorine, chlorine, bromine, nitro, cyano, $C_1-C_4$-alkylthio, $C_1-C_4$-alkoxy, $C_1-C_4$-halogenoalkoxy, $C_1-C_4$-halogenoalkylthio, $C_1-C_4$alkyl or $C_1$ $-C_4$-halogenoalkyl, $R^3$ represents optionally fluorine-, chlorine-, bromine-substituted $C_1-C_{10}$-alkyl, or represents phenyl or benzyl each of which is substituted by fluorine, chlorine, $C_1-C_4$-alkyl or $C_1-C_4$-alkoxy, or the enantiomerically pure form thereof.

4. A compound according to claim 1, in which

X represents methyl, ethyl, propyl, isopropyl, fluorine, chlorine, bromine or methoxy, Y represents hydrogen, methyl, ethyl, propyl, isopropyl, butyl, isobutyl, tert-butyl, fluorine, chlorine, bromine, methoxy, ethoxy and trifluoromethyl, Z represents methyl, ethyl, propyl, isopropyl, butyl, isobutyl, tert-butyl, fluorine, chlorine, bromine, methoxy and ethoxy, n represents 1, Het represents a heterocyclic group selected from the group consisting of

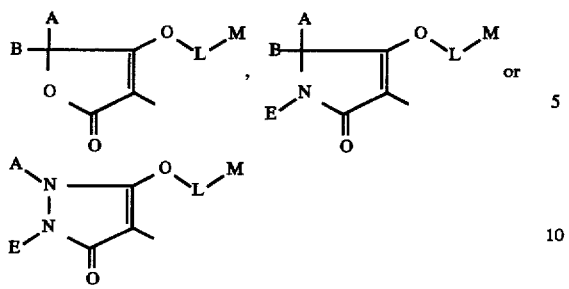

in which

A and B are identical or different and represent hydrogen, in each case optionally fluorine- or chlorine-substituted straight-chain or branched $C_1$–$C_8$-alkyl, $C_3$–$C_4$-alkenyl, $C_1$–$C_6$-alkoxy-$C_2$–$C_4$-alkyl, $C_1$–$C_4$-polyalkoxy-$C_2$–$C_4$-alkyl, $C_1$–$C_6$-alkylthio-$C_2$–$C_4$-alkyl, cycloalkyl having 3 to 6 ring atoms, which can be interrupted by 1-2 oxygen and/or sulphur atoms, or phenyl, pyridinyl, imidazolyl, indolyl or phenyl-$C_1$–$C_3$-alkyl each of which is optionally substituted by fluorine, chlorine, methyl, ethyl, propyl, isopropyl, methoxy, ethoxy, trifluoromethyl or nitro, or in which A and B, together with the carbon atom to which they are attached, form a saturated or unsaturated 3- to 8-membered ring which is optionally interrupted by oxygen and/or sulphur and is optionally substituted by fluorine, chlorine, $C_1$–$C_4$-alkyl, $C_1$–$C_4$ alkoxy, trifluoromethyl, $C_1$–$C_2$-alkylthio or phenyl which is optionally substituted by fluorine, chlorine, methyl, methoxy, E represents hydrogen or in each case optionally fluorine- or chlorine-substituted straight-chain or branched $C_1$–$C_8$-alkyl, $C_3$–$C_4$-alkenyl, $C_1$–$C_6$-alkoxy-$C_2$–$C_4$-alkyl, $C_1$–$C_4$-polyalkoxy-$C_2$–$C_4$-alkyl, $C_1$–$C_6$-alkylthio-$C_2$–$C_4$-alkyl, cycloalkyl having 3 to 6 ring atoms, which can be interrupted by 1-2 oxygen and/or sulphur atoms, or represents phenyl, pyridinyl, imidazolyl, indolyl or phenyl-$C_1$–$C_3$-alkyl which is optionally substituted by fluorine, chlorine, methyl, ethyl, propyl, isopropyl, methoxy, ethoxy, trifluoromethyl or nitro, or in which A and E, together with the atoms to which they are attached, form a saturated or unsaturated 3- to 8-membered ring which is optionally interrupted by oxygen and/or sulphur and is optionally substituted by fluorine, chlorine, $C_1$–$C_4$-alkyl, $C_1$–$C_4$-alkoxy, trifluoromethyl, $C_1$–$C_2$-alkylthio or phenyl which is optionally substituted by fluorine, chlorine, methyl, methoxy, or, if Het in formula (I) represents a pyrazolinone ring, A and E, together with the two nitrogen atoms of the pyrazoline ring, represent a group of the formulae 1 or 2 listed below which is optionally monosubstituted to trisubstituted by identical or different substituents consisting of methyl, fluorine or chlorine,

L represents one of the following groups,

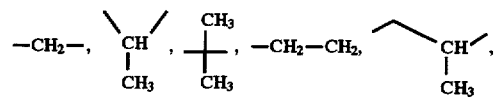

M represents one of the following groups:

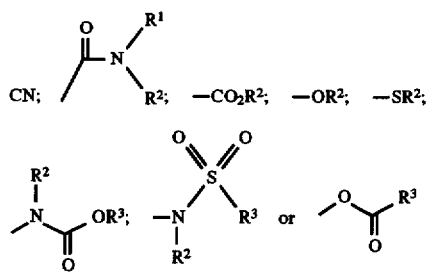

$R^1$ represents hydrogen or $C_1$–$C_8$-alkyl, $R^2$ represents in each case optionally fluorine-, chlorine-, bromine-substituted $C_1$–$C_8$-alkyl, $C_3$–$C_4$-alkenyl, $C_3$–$C_4$-alkinyl, cyclopropyl, cyclopentyl, cyclohexyl, $C_1$–$C_6$-alkoxy-$C_2$–$C_4$-alkyl, $C_1$–$C_6$-alkylthio-$C_2$–$C_4$-alkyl, or represents phenyl or benzyl each of which is optionally substituted by fluorine, chlorine, bromine, nitro, cyano, methylthio, ethylthio, methoxy, ethoxy, trifluoromethylthio, trifluoromethoxy, methyl, ethyl, trifluoromethyl, or the enantiomerically pure form thereof.

5. A process for the preparation of the substituted aryl keto-enolic heterocycle according to claim 1, wherein in order to obtain a compound of the formula (Ia),

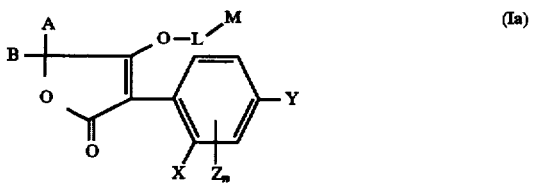 (Ia)

in which

A, B, L, M, X, Y, Z and n have the meaning given in claim 11, a compound of the formula (IIa)

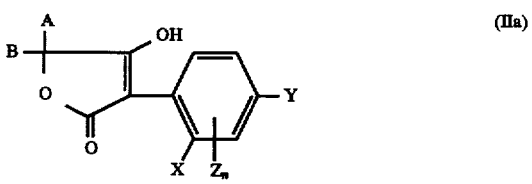 (IIa)

in which

A, B, X, Y, Z and n have the meaning given in claim 11 is reacted with compounds of the formula (III)

G—L—M (III)

in which
L and M have the meaning given in claim 11
and
G represents a leaving group, in the presence of a diluent and in the presence of a base;
(B) in order to obtain compounds of the formula (Ib)

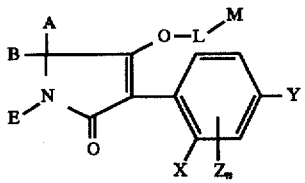

(Ib)

in which
A, B, E, L, M, X, Y, Z and n have the meaning in claim 11 a compound of the formula (IIb)

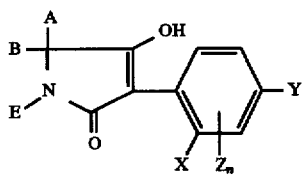

(IIb)

in which
A, B, E, X, Y, Z and n have the meaning in, claim 11 is reacted with compounds of the formula (III)

G—L—M  (III)

in which
L and M have the meaning given above
and
G represents a leaving group in the presence of a diluent and in the presence of a base; and
(C) in order to obtain a compound of the formula (Ic)

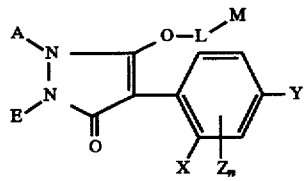

(Ic)

in which
A, E, L, M, X, Y, Z and n have the meaning given in claim 1 a compound of the formula (IIc)

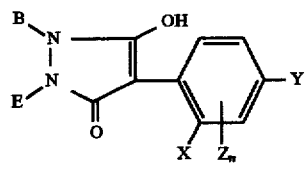

(IIc)

in which
B, E, X, Y, Z and n have the meaning given in claim 1 is reacted with a compound of the formula (III)

G—L—M  (III)

in which
L and M have the meaning given above
and
G represents a leaving group in the presence of a diluent and in the presence of a base.

6. A compound according to claim 1, wherein Het is

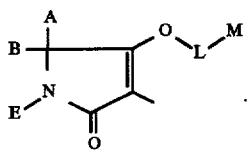

7. A compound according to claim 1, wherein Het is

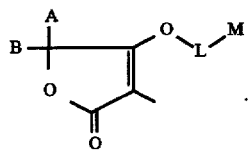

8. A compound according to claim 1, wherein Het is

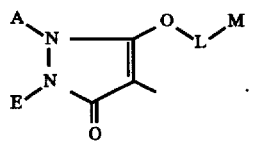

9. A pesticidal or herbicidal composition which comprises a peticidally or herbicidally effective amount of a compound according to claim 1 and an inert carrier.

10. A method of combatting pests in plant protection, the household sector and in the protection of stored products which comprises apply to said pests or to a habitate to which they reside an effective amount of a compound according to claim 1.

11. The method according to claim 8 wherein the pest is an arthropod or a phytopantogenic fungi.

12. A method of combatting unwanted plant growth which comprises applying to the unwanted plant or to an environment where it resides, an effective amount of a compound according to claim 1.

13. A process for preparing a pesticidal composition which comprises mixing a compound according to claim 1 with an extender or a surface-active agent.

* * * * *